(12) United States Patent
Koda

(10) Patent No.: US 10,625,298 B2
(45) Date of Patent: Apr. 21, 2020

(54) DIP COATING DEVICE AND METHOD FOR PRODUCING COATED MEMBER

(71) Applicant: KANEKA CORPORATION, Osaka-shi, Osaka (JP)

(72) Inventor: Takuro Koda, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 182 days.

(21) Appl. No.: 15/570,253

(22) PCT Filed: Feb. 26, 2016

(86) PCT No.: PCT/JP2016/055935
§ 371 (c)(1),
(2) Date: Oct. 27, 2017

(87) PCT Pub. No.: WO2016/174913
PCT Pub. Date: Nov. 3, 2016

(65) Prior Publication Data
US 2018/0141079 A1 May 24, 2018

(30) Foreign Application Priority Data
Apr. 28, 2015 (JP) ................................. 2015-092285

(51) Int. Cl.
*B05D 1/18* (2006.01)
*B05C 3/09* (2006.01)
(Continued)

(52) U.S. Cl.
CPC .................. *B05D 1/18* (2013.01); *B05C 3/09* (2013.01); *B05C 13/025* (2013.01); *B05D 1/36* (2013.01);
(Continued)

(58) Field of Classification Search
CPC .................................. B05D 3/02; A61B 18/14
See application file for complete search history.

(56) References Cited

U.S. PATENT DOCUMENTS

| 4,987,851 A | 1/1991 | Yasuda et al. |
| 5,558,900 A * | 9/1996 | Fan ........................ A61L 29/049 427/2.28 |
| 2003/0125679 A1 | 7/2003 | Kubota et al. |

FOREIGN PATENT DOCUMENTS

| JP | 53-90377 A | 8/1978 |
| JP | 56-17658 A | 2/1981 |

(Continued)

OTHER PUBLICATIONS

International Search Report for PCT/JP2016/055935 (PCT/ISA/210) dated May 31, 2016.
(Continued)

*Primary Examiner* — Dah-Wei D. Yuan
*Assistant Examiner* — Andrew J Bowman
(74) *Attorney, Agent, or Firm* — Birch, Stewart, Kolasch & Birch, LLP

(57) ABSTRACT

Provided are a dip coating device which minimizes attachment of a coating material to a member to which a member to be coated is fixed, thereby facilitating coating of the member to be coated and a method for producing a coated member which is obtained by dip coating a member to be coated with a coating material. The dip coating device 10 of the present invention for coating a member to be coated 20 with a coating material 70, comprises a reservoir 30 that stores a coating material 70, a first fixing part 40 that holds a member to be coated 20, and a second fixing part 50 directly or indirectly provided on a wall 31 of the reservoir 30, wherein the first fixing part 40 and the second fixing part 50 magnetically attract to each other.

18 Claims, 11 Drawing Sheets

(51) Int. Cl.
  *B05C 13/02*    (2006.01)
  *B05D 1/36*    (2006.01)
  *B05D 1/42*    (2006.01)
  A61M 25/10    (2013.01)
  A61M 25/00    (2006.01)
  B05D 3/04    (2006.01)

(52) U.S. Cl.
  CPC ........... *B05D 1/42* (2013.01); *A61M 25/0009* (2013.01); *A61M 25/1027* (2013.01); *B05D 3/0486* (2013.01)

(56) References Cited

FOREIGN PATENT DOCUMENTS

| JP | 62-126028 A | 6/1987 | | |
|---|---|---|---|---|
| JP | 63-82470 U | 5/1988 | | |
| JP | U1-S63-082470 | * 5/1988 | ............... | A61B 5/04 |
| JP | 2-152573 A | 6/1990 | | |
| JP | 9-24580 A | 1/1997 | | |
| JP | 9-234407 A | 9/1997 | | |
| JP | 2001-178825 A | 7/2001 | | |
| JP | 2010-189210 A | 9/2010 | | |
| JP | 2013-192885 A | 9/2013 | | |
| JP | 2015-65986 A | 4/2015 | | |

OTHER PUBLICATIONS

Written Opinion of the International Searching Authority for PCT/JP2016/055935 (PCT/ISA/237) dated May 31, 2016.

* cited by examiner

[Fig. 1]
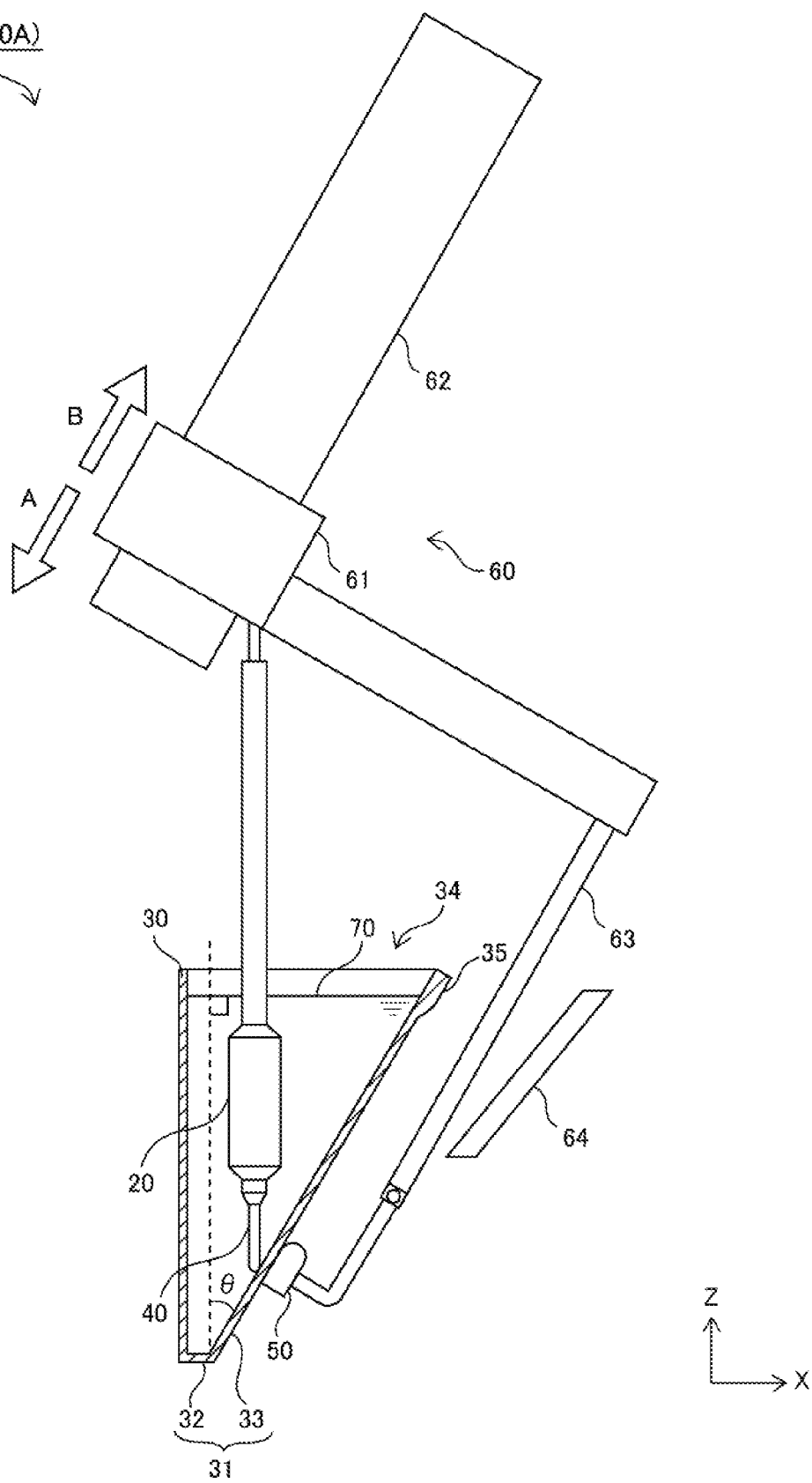

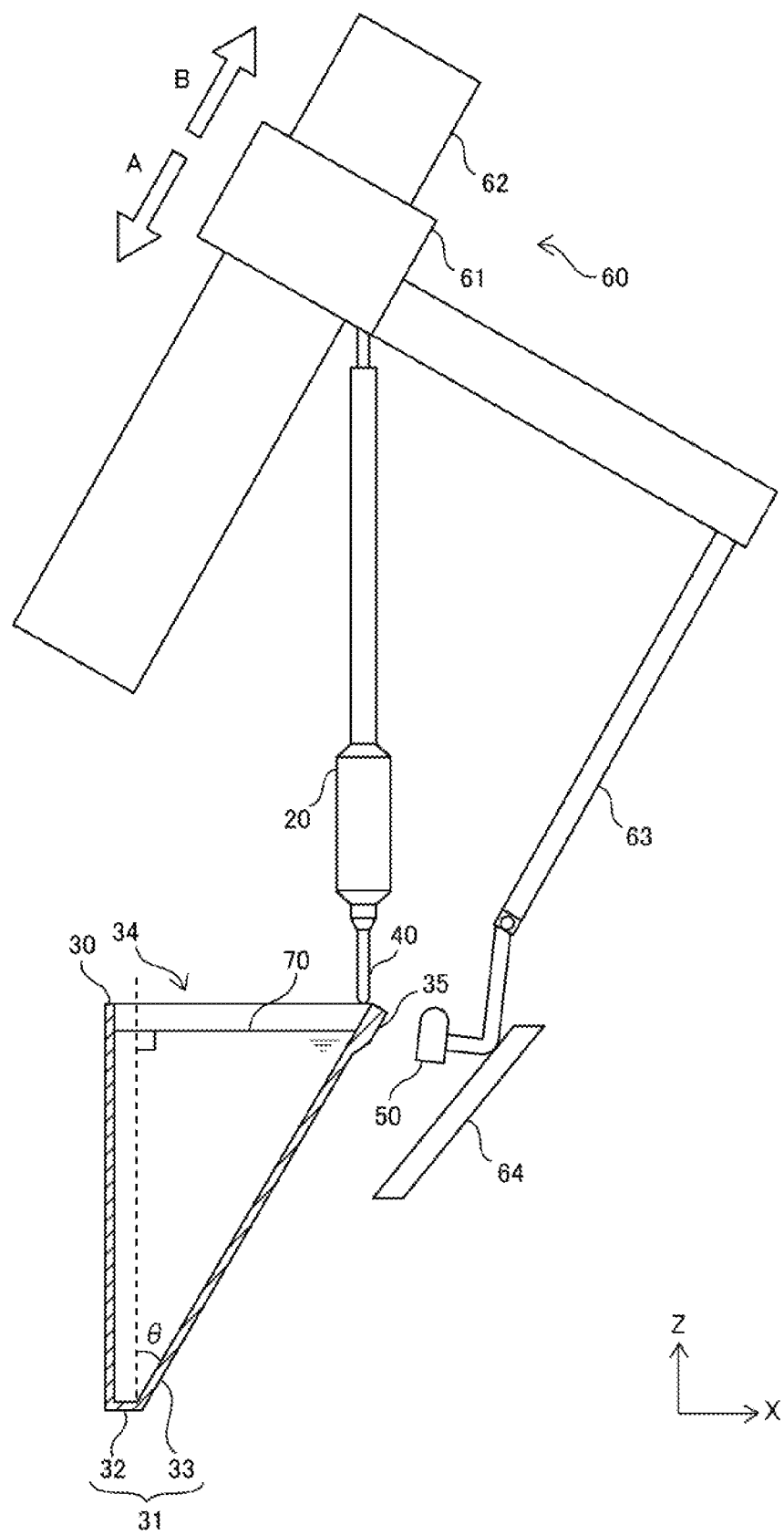
[Fig. 2]

[Fig. 3]
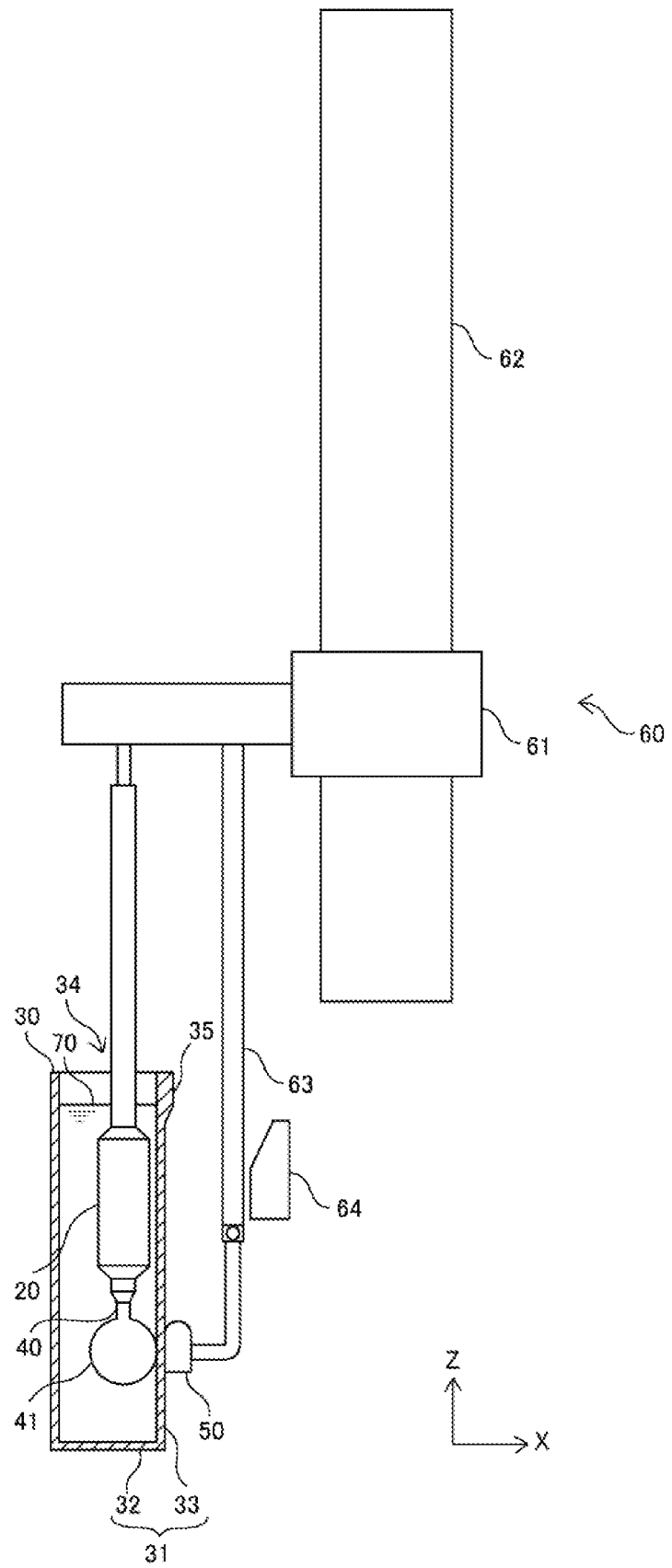

[Fig. 4]
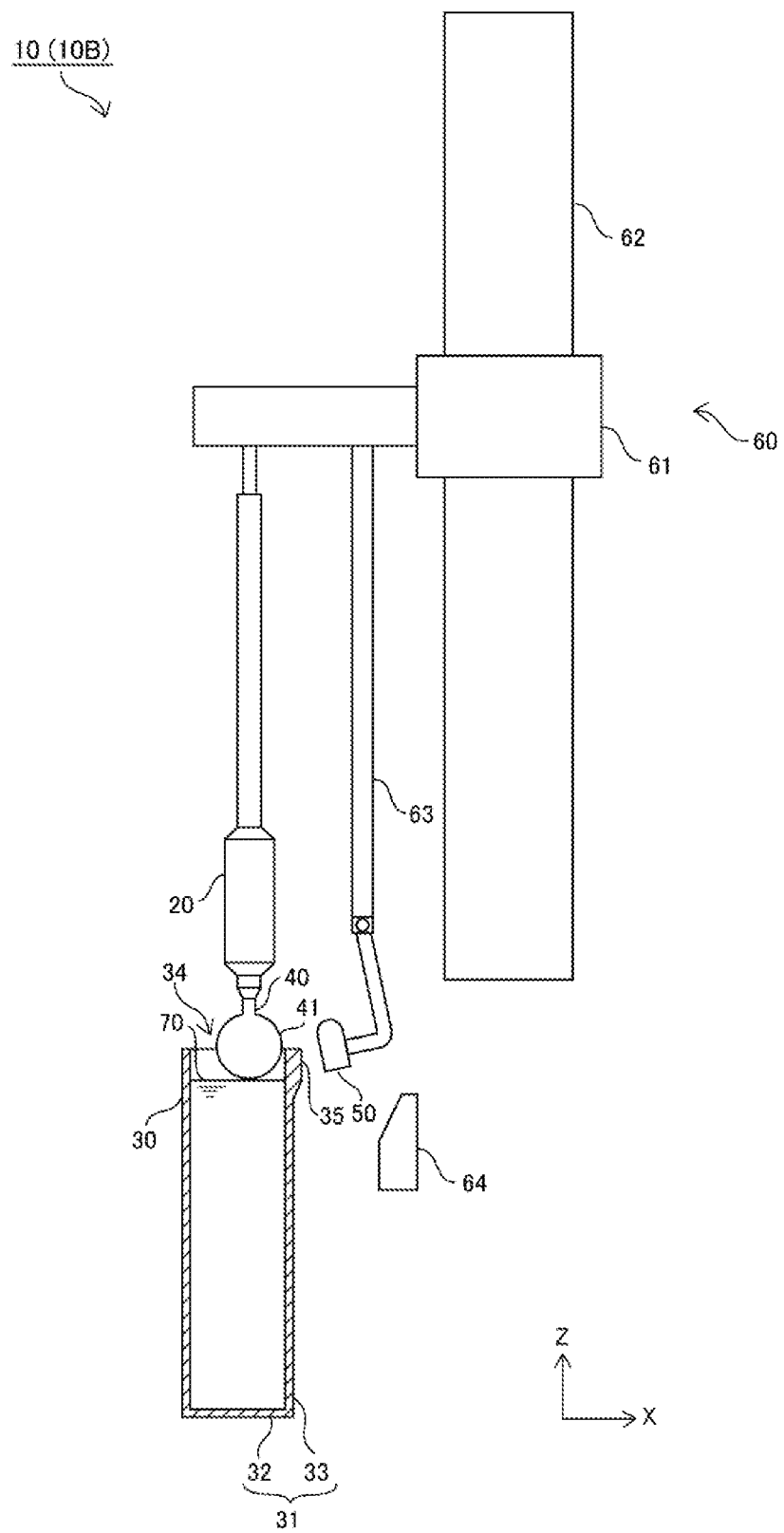

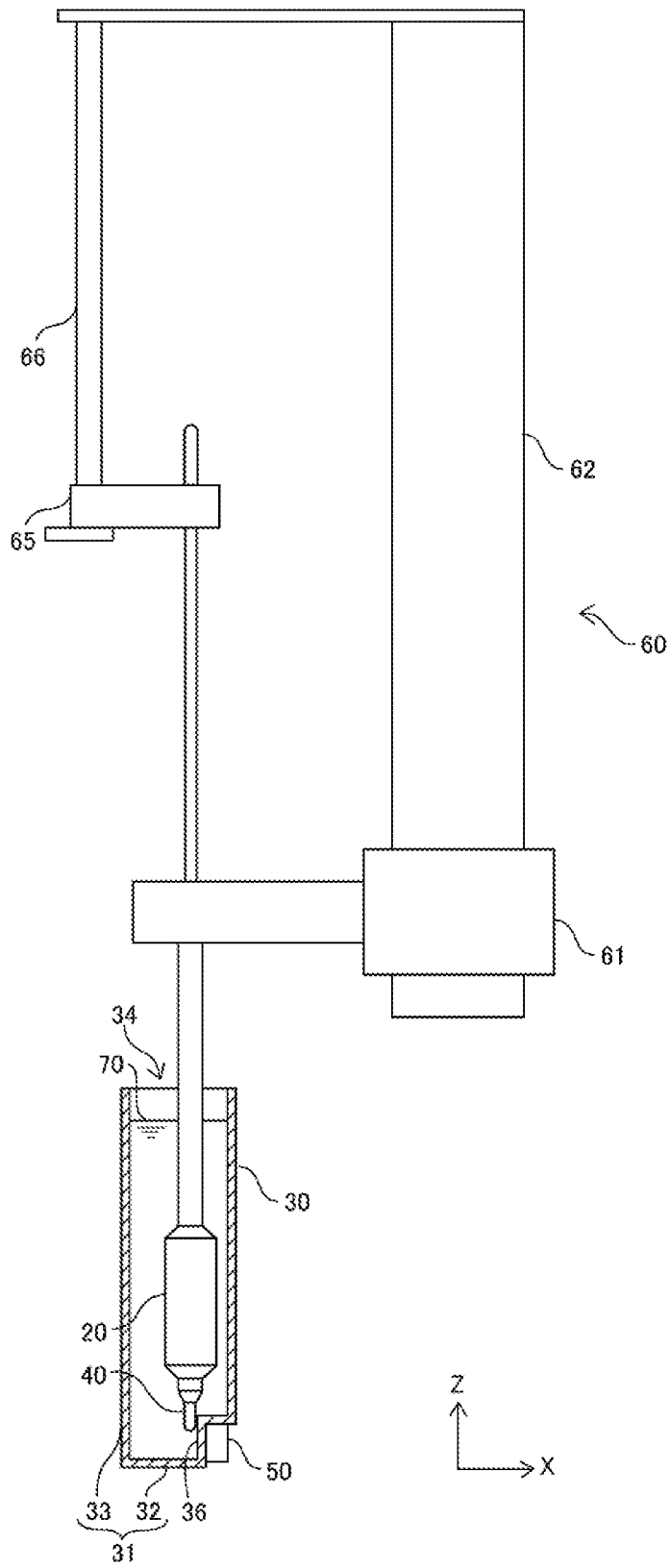
[Fig. 5]

[Fig. 6]
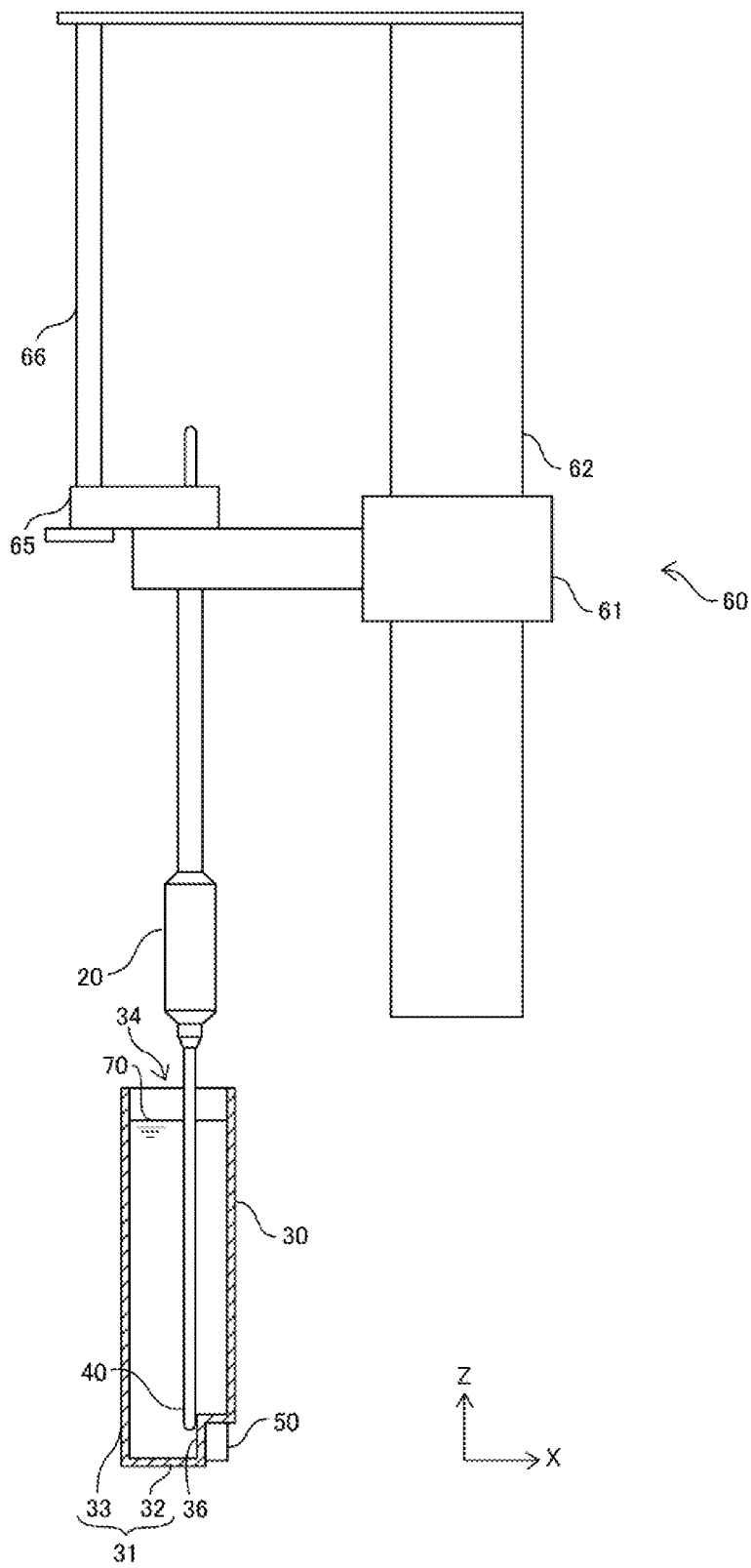

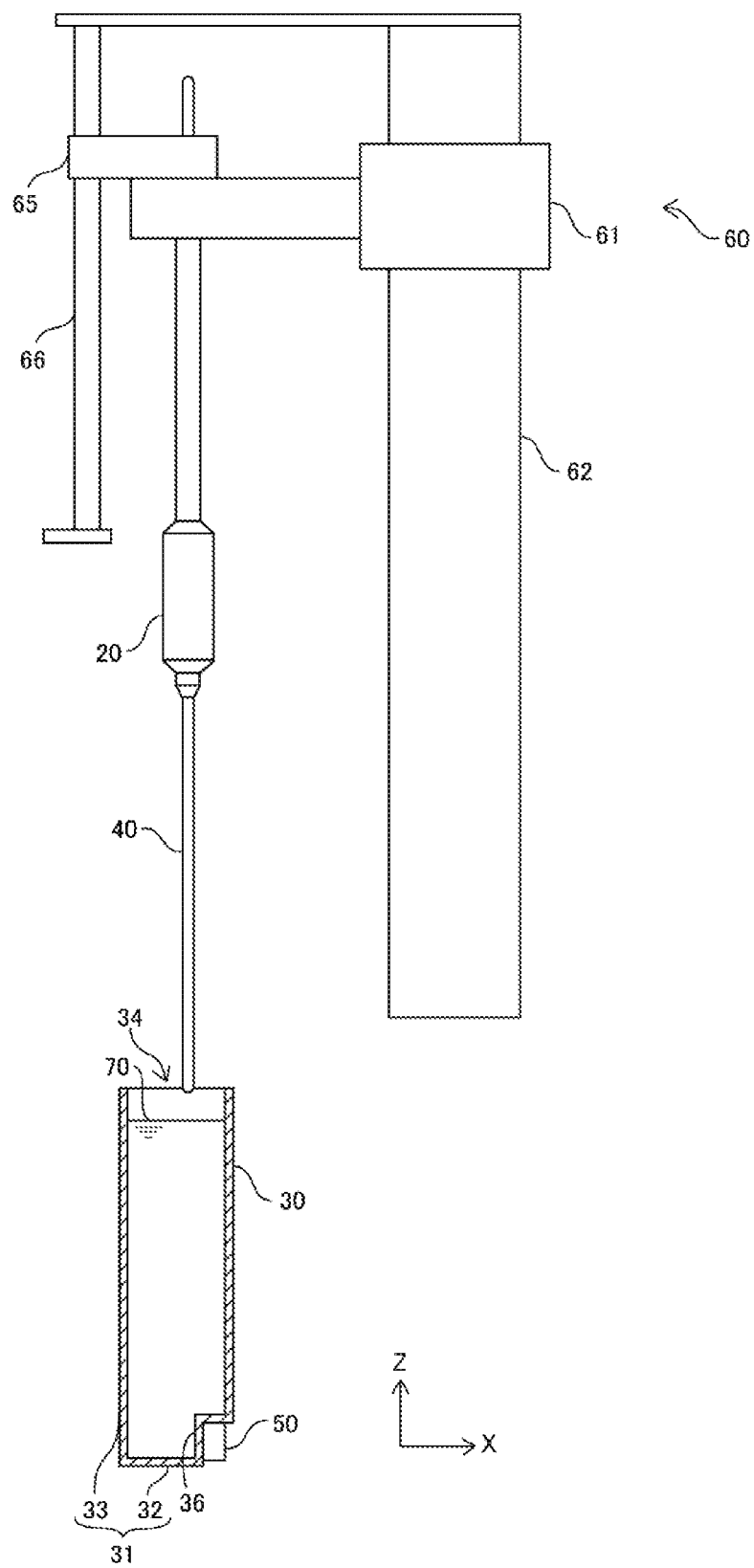
[Fig. 7]

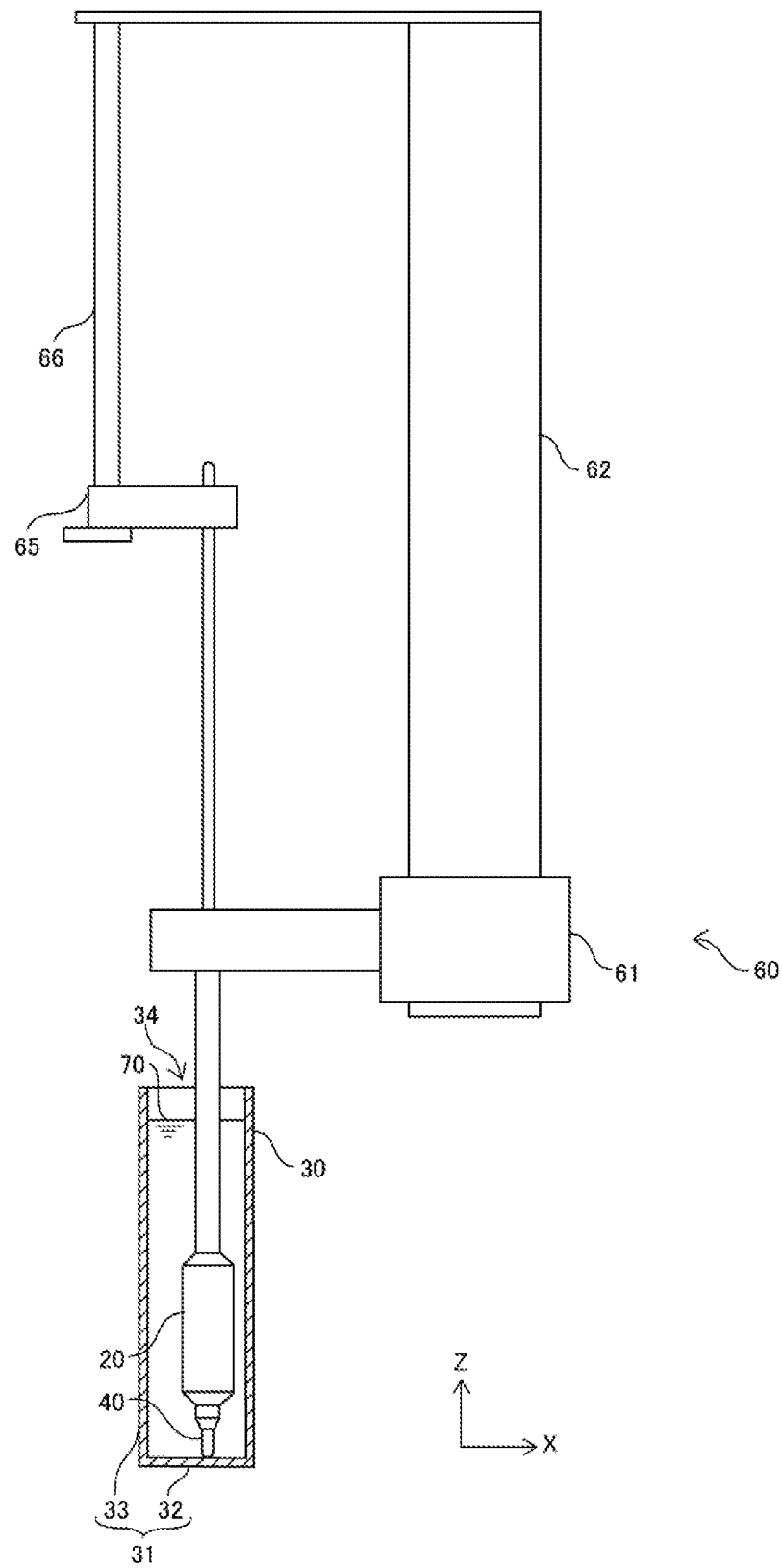
[Fig. 8]

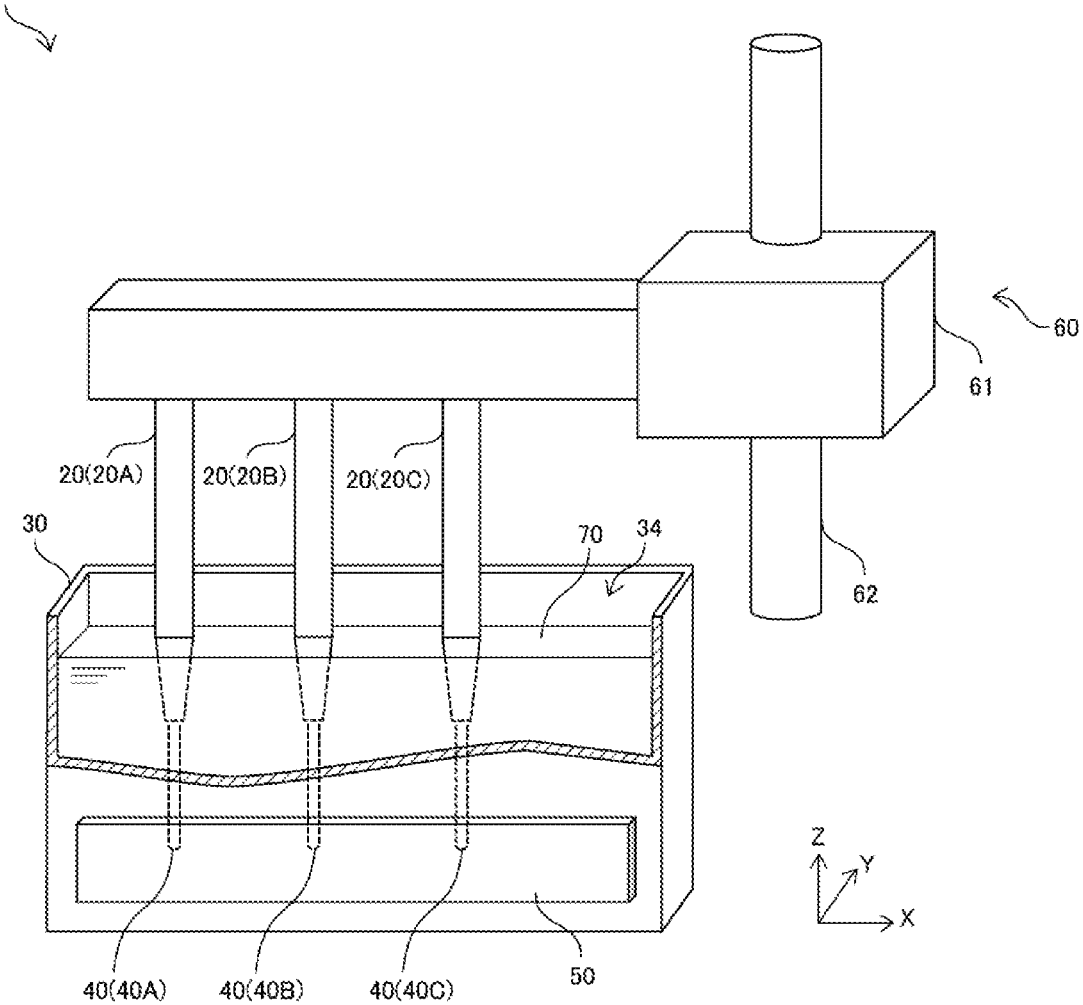

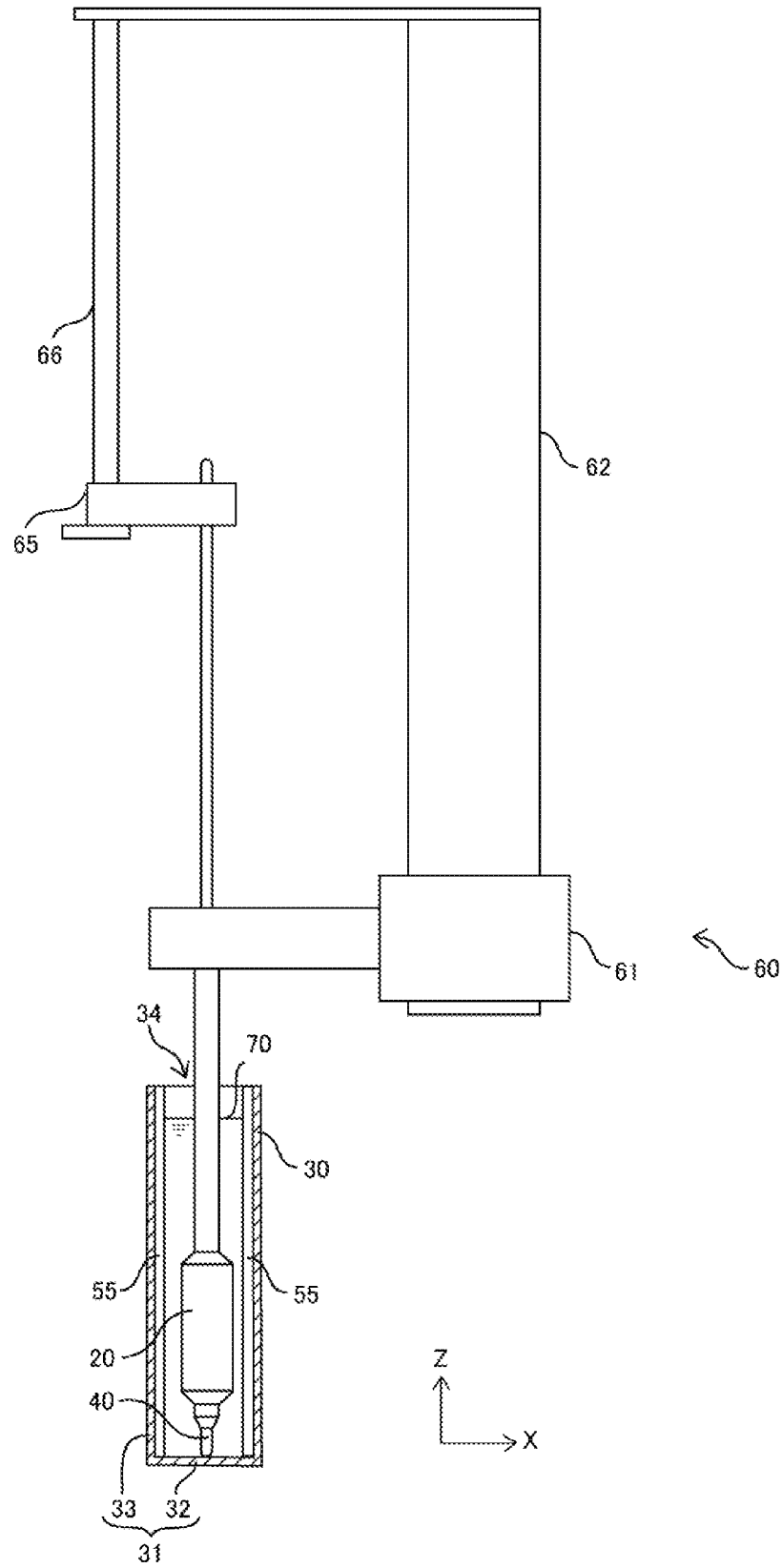

[Fig. 11]
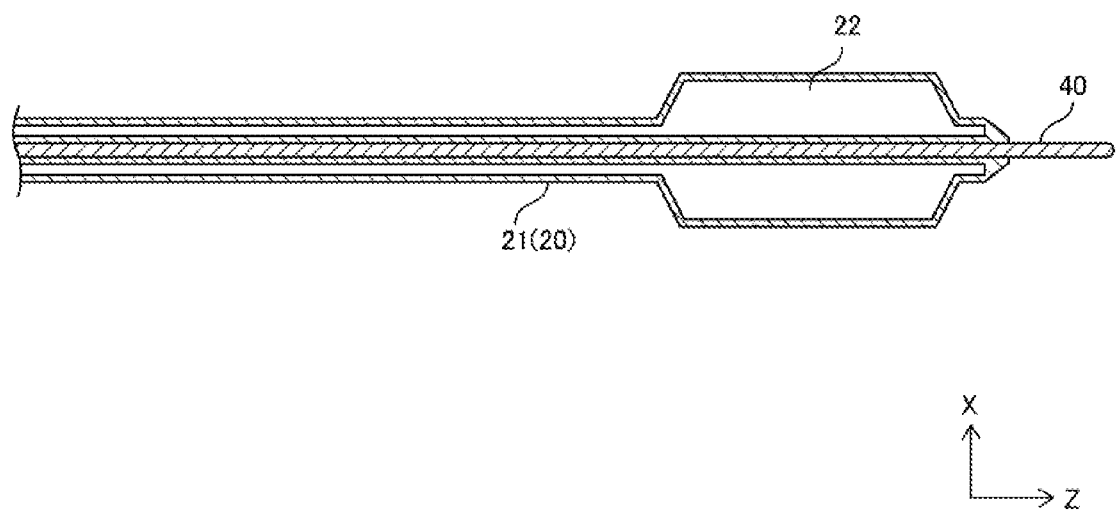

DIP COATING DEVICE AND METHOD FOR PRODUCING COATED MEMBER

TECHNICAL FIELD

The present invention relates to a dip coating device capable of coating a member to be coated with a coating material, and a method for producing a coated member which is obtained by coating a member to be coated with a coating material.

BACKGROUND ART

Ordinary coating application methods include dip coating, brushing, non-electrostatic spray coating, and electrostatic spray coating. Performances of coating methods can be compared and evaluated with various indexes such as coating efficiency (dose to a coating-required part (g)/actual application amount (g)), area productivity, application speed, coating film uniformity, amount of generated waste, and cost.

Dip coating is a method of dipping a member to be coated into a tank which stores a liquid coating material and pulling up the same. Dip coating is widely used because dip coating enables a coating material to be uniformly coated on a member to be coated to accordingly have high coating efficiency or area productivity, prevents foreign matters from easily entering a coating material compared with brushing, and involves less nozzle clogging which is caused in spray coating.

For example, Patent Literature 1 recites a coating device for coating an outer surface of a glass container with a coating liquid, the coating device having a dip tank, an endless transport conveyor which rotatably grasps the glass container and transports the same, and a rotation imparting part which comes into contact with an outer circumference surface of a roller part of the conveyor to rotate the glass container.

Patent Literature 2 recites a coating material coating method and a coating device in which only a half of a cylindrical metal part is coated and then the remaining half is coated to enable treatment without attaching a paint to a jig which supports the cylindrical metal part.

Additionally, for coating an outer surface of a tubular body, a conventionally used dip coating device has, for example, a comb-shaped fixing member, a supporting member which engages with a front end of the fixing member, and a reservoir which stores a coating material. With such a device, coating of the tubular body with the coating material is conducted by inserting the tubular body into the comb-shaped fixing member and engaging the front end of the fixing member exposed from the tubular body with the supporting member, and then dipping the fixing member, the supporting member, and the tubular body together into the reservoir which stores the coating material.

CITATION LIST

Patent Literature

Patent Literature 1
  Japanese Unexamined Patent Application Publication No. 2010-189210
Patent Literature 2
  Japanese Unexamined Patent Application Publication No. H09-234407

SUMMARY OF INVENTION

Technical Problem

In the coating device of Patent Literature 1, in a case, for example, where a member to be coated is a glass bottle having large buoyancy, as a result of moving in a coating material (coating liquid), the member to be coated might come into contact with other member to be coated or with an inner wall of the dip tank to cause a coating failure.

The coating material coating method and the coating device of Patent Literature 2 have difficulty in application to a case where a member to be coated is a tubular body with a small outer diameter, and two coating operations are required for one member to be coated, which has difficulty in increasing productivity. Additionally, coating operation is conducted as two separate operations, and thus a coated film might have a non-uniform film thickness near a boundary between two coating ranges.

Additionally, a conventional dip coating device has a room for improvement in working efficiency because before and after dipping a tubular body into a coating material, engagement between, for example, a comb-shaped fixing member and a supporting member and releasing operation thereof are required. Additionally, another concern is reduction in coating efficiency because a coating material is attached not only to a tubular body as a member to be coated but also to a supporting member originally requiring no coating for each dipping operation of the tubular body.

An object of the present invention, which has been made in view of the above circumstances, is to provide a dip coating device which minimizes attachment of a coating material to a member to which a member to be coated is fixed, thereby facilitating coating of the member to be coated, and a method for producing a coated member which is obtained by dip coating a member to be coated with a coating material.

Solution to Problem

A dip coating device of the present invention which is able to achieve the above object, for coating a member to be coated with a coating material, comprises a reservoir that stores a coating material, a first fixing part that holds a member to be coated, and a second fixing part directly or indirectly provided on a wall of the reservoir, wherein the first fixing part and the second fixing part magnetically attract to each other. In the dip coating device of the present invention, a magnetic attractive force acts between the first fixing part which holds the member to be coated and the second fixing part provided on the wall of the reservoir, the member to be coated is attracted to the second fixing part so as to be fixed in the reservoir. Accordingly, in the dip coating device of the present invention, even when the member to be coated receives buoyancy in the coating material within the reservoir, the member to be coated remains fixed to the second fixing part while being held by the first fixing part, so that the member to be coated hardly moves within the reservoir. Additionally, the dip coating device of the present invention suppresses attachment of a coating material to a supporting member which engages with, for example, a comb-shaped fixing member for each dipping operation of a member to be coated as in a conventional dip coating device, resulting in increasing a utilization ratio of the coating material.

A dip coating device of the present invention for coating a member to be coated with a coating material, may comprise a reservoir that stores a coating material, a first fixing member that holds a member to be coated, and a second fixing member directly or indirectly provided on a wall of the reservoir, wherein the first fixing member and the second fixing member magnetically attract to each other. In other words, the first fixing part and the second fixing part may be fixing members. Specifically, the first fixing part may be provided on the first fixing member and the second fixing part may be provided on the second fixing member.

In the dip coating device of the present invention, the reservoir and the second fixing part are preferably integrally formed. This generates a magnetic attractive force between the first fixing part and the reservoir to enable simplification of a structure of the device.

In the dip coating device of the present invention, the reservoir preferably has a first cross section with an inner diameter larger than an inner diameter of a second cross section on a side closer to a bottom wall in relation to the first cross section, the first cross section being parallel to a liquid surface of the coating material and close to the liquid surface. This allows an opening part of the reservoir to have an increased area, the opening part serving for dipping the member to be coated into the coating material or for pulling up the member to be coated from the coating material. As a result, the dip coating device of the present invention allows a spaced distance between the member to be coated and the side wall to be increased, so that the member to be coated and the side wall hardly come into contact with each other. This suppresses generation of a coating failure of the member to be coated due to contact between the member to be coated and the side wall.

In the dip coating device of the present invention, a part of a side wall of the reservoir is preferably inclined with respect to a direction perpendicular to a liquid surface of the coating material. When the side wall of the reservoir is inclined, the opening part of the reservoir can be increased in an area, the opening part serving for dipping the member to be coated into the coating material or for pulling up the member to be coated from the coating material. As a result, the dip coating device of the present invention allows a spaced distance between the member to be coated and the side wall to be increased, so that the member to be coated and the side wall hardly come into contact with each other. This suppresses generation of a coating failure of the member to be coated due to contact between the member to be coated and the side wall.

The first fixing part preferably has a bar shape. This prevents the coating member from being crimpled and enables the same to be fixed when the coating member is a tubular body. Additionally, the first fixing member preferably has a bar shape and has an outer diameter at one end part thereof larger than an outer diameter at the other end part thereof. As a result, even when the first fixing member comes close to the side wall, the one end part having a relatively large outer diameter first comes into contact with the side wall of the reservoir, so that a spaced distance between the member to be coated and the side wall can be ensured to a certain extent. The member to be coated is accordingly less likely to come into contact with the side wall, resulting in preventing generation of a coating failure due to contact between the member to be coated and the side wall.

In the dip coating device of the present invention, the first fixing part is preferably provided with a bulge part projecting toward a side wall of the reservoir. This makes a bulge part projecting toward the side wall of the first fixing part first comes into contact with the side wall of the reservoir even when the first fixing part comes close to the side wall. The dip coating device of the present invention is therefore allowed to ensure a spaced distance between the member to be coated and the side wall to a certain extent, so that the member to be coated is less likely to come into contact with the side wall, resulting in preventing generation of a coating failure due to contact between the member to be coated and the side wall.

In the dip coating device of the present invention, a side wall of the reservoir preferably has a thick part. Since this enables reduction in intensity of a magnetic attractive force acting between the first fixing part and the second fixing part in a thick part of the side wall of the reservoir, the first fixing part and the second fixing part can be smoothly pulled away to make it easy to take out the member to be coated and the first fixing part from the reservoir.

The thick part is preferably formed so as to become thicker from a lower part of the reservoir toward an upper part of the reservoir in a direction perpendicular to a liquid surface of the coating material. This enables the first fixing part and the second fixing part to be more smoothly pulled away.

In the dip coating device of the present invention, a side wall of the reservoir is preferably provided with a projection part projecting toward inside of the reservoir. This facilitates the projection part projecting toward inside of the reservoir to first come into contact with the reservoir even when the first fixing part comes close to the side wall of the reservoir. Since it is therefore possible to ensure a spaced distance between the member to be coated and the side wall to a certain extent, the member to be coated is less likely to come into contact with the side wall, resulting in preventing a coating failure due to contact between the member to be coated and the side wall.

In the dip coating device of the present invention, at least one of the first fixing part and the second fixing part is preferably provided with a magnet. When at least one of the first fixing part and the second fixing part is provided with a magnet, a magnetic attractive force can be generated between the first fixing part and the second fixing part.

In the dip coating device of the present invention, the magnet is preferably an electromagnet. In a case where the magnet is an electromagnet, intensity of the magnetic attractive force can be adjusted.

In the dip coating device of the present invention, it is preferable that a side wall of the reservoir is provided with a buffer member and the first fixing part and the buffer member magnetically repel each other. This enables reduction in a risk that in a region where a buffer member is provided, the first fixing part comes into contact with the reservoir.

It is preferable that a plurality of the first fixing parts which are arranged in parallel with each other holds a plurality of the members to be coated which are preferably arranged in parallel with each other respectively. By configuring the first fixing part in this manner, the dip coating device of the present invention enables coating, with a coating material, of even a plurality of members to be coated provided in parallel to each other.

In the present invention, the member to be coated is preferably a medical tubular body. Additionally, the dip coating device of the present invention can be preferably used even when the medical tubular body is a medical catheter. Since the dip coating device of the present invention enables coating of a member to be coated with ease, productivity of a medical tubular body or a medical catheter can be increased. Further, the dip coating device of the present invention can be preferably used even when the medical catheter is a balloon catheter. This is because the dip coating device of the present invention can be suitably used even when a member to be coated is a tubular body having large buoyancy.

The present invention is preferably a medical tubular body produced by the above dip coating device. Since a medical tubular body produced by the above dip coating device is uniformly coated with a coating material, the coating material fully exhibits function thereof, and an effect of protecting the tubular body by a coated film is also expected.

Further, the present invention is a method for producing a coated member obtained by dip coating a member to be coated with a coating material, comprising the steps of: fixing a member to be coated to a first fixing part; dipping the member to be coated into a reservoir in which a coating material is stored; moving the first fixing part close to a second fixing part which is directly or indirectly provided on a wall of the reservoir and capable of generating a magnetic attractive force with the first fixing part; separating the first fixing part from the second fixing part; and pulling up the member to be coated out of the reservoir in which the coating material is stored. Since the method for producing a coated member of the present invention includes a step of moving the first fixing part which fixes the member to be coated close to the second fixing part capable of generating a magnetic attractive force with the first fixing part, the second fixing part being provided directly or indirectly on the wall of the reservoir, the member to be coated which is fixed to the first fixing part is attracted to the second fixing part and fixed in the reservoir. Accordingly, even when the member to be coated is susceptible to buoyancy, the first fixing part attracts the second fixing part while the member to be coated remains fixed, and thus the member to be coated hardly moves within the reservoir. Additionally, the method for producing a coated member of the present invention suppresses attachment of a coating material to a supporting member which engages with, for example, a comb-shaped fixing member for each dipping operation of a member to be coated as in a conventional dip coating method, resulting in increasing a utilization ratio of the coating material.

In the method for producing a coated member of the present invention, it is preferable that at least one of the first fixing part and the second fixing part is provided with a electromagnet and the method further comprises the step of generating a magnetic attractive force between the first fixing part and the second fixing part by the electromagnet after the step of moving the first fixing part close to the second fixing part. When at least one of the first fixing part and the second fixing part is provided with a magnet, intensity of a magnetic attractive force can be adjusted. Additionally, by generating a magnetic attractive force after the step of moving the first fixing part close to the second fixing part, it is possible to suppress the first fixing part and the second fixing part from being attracted to each other while a distance between the first fixing part and the second fixing part is drastically reduced. This enables reduction in shock or vibration to be applied to a coating material, so that a thickness of a coating material to be coated on a member to be coated can be uniform.

In the method for producing a coated member of the present invention, it is preferable that the member to be coated is a tubular body and the first fixing part is inserted into a lumen of the tubular body in the step of fixing the member to be coated to the first fixing part. Since inserting the first fixing part into the lumen of the tubular body prevents the coating material from easily entering the lumen of the tubular body, attachment of the tubular body to the lumen of the tubular body can be suppressed.

Advantageous Effects of Invention

In the dip coating device and the method for producing a coated member of the present invention, the member to be coated is attracted to the second fixing part so as to be fixed in the reservoir. Accordingly, even when the member to be coated receives buoyancy in the coating material within the reservoir, the member to be coated remains fixed to the second fixing part while being held by the first fixing part, so that the member to be coated hardly moves within the reservoir. Additionally, this suppresses attachment of a coating material to a supporting member which engages with, for example, a comb-shaped fixing member for each dipping operation of a member to be coated as in a conventional dip coating device, resulting in increasing a utilization ratio of the coating material.

BRIEF DESCRIPTION OF THE DRAWINGS

FIG. 1 is a side view (a partial cross-sectional view) of the dip coating device according to a first embodiment of the present invention.

FIG. 2 is a side view (a partial cross-sectional view) of the dip coating device according to a first embodiment of the present invention.

FIG. 3 is a side view (a partial cross-sectional view) of the dip coating device according to a second embodiment of the present invention.

FIG. 4 is a side view (a partial cross-sectional view) of the dip coating device according to a second embodiment of the present invention.

FIG. 5 is a side view (a partial cross-sectional view) of the dip coating device according to a third embodiment of the present invention.

FIG. 6 is a side view (a partial cross-sectional view) of the dip coating device according to a third embodiment of the present invention.

FIG. 7 is a side view (a partial cross-sectional view) of the dip coating device according to a third embodiment of the present invention.

FIG. 8 is a side view (a partial cross-sectional view) of the dip coating device according to a fourth embodiment of the present invention.

FIG. 9 is a perspective view (a partial cross-sectional view) of the dip coating device according to a fifth embodiment of the present invention.

FIG. 10 is a side view (a partial cross-sectional view) of the dip coating device according to a sixth embodiment of the present invention.

FIG. 11 is a cross-sectional view showing an example in which a first fixing part is inserted into a lumen of a tubular body which is a member to be coated.

DESCRIPTION OF THE EMBODIMENTS

Embodiments of the present invention will be specifically explained below, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

In the present invention, the dip coating device has an up-down direction and a right-left direction. A Z direction in the figures of the present application corresponds to the up-down direction of the dip coating device, and an X-Y direction in the figures of the present application corresponds to a direction parallel to a liquid surface of a coating material.

1. Dip Coating Device

A dip coating device of the present invention for coating a member to be coated with a coating material, comprises a reservoir that stores a coating material, a first fixing part that holds a member to be coated, and a second fixing part directly or indirectly provided on a wall of the reservoir, wherein the first fixing part and the second fixing part magnetically attract to each other. In the dip coating device of the present invention, a magnetic attractive force acts between the first fixing part which holds the member to be coated and the second fixing part provided on the wall of the reservoir, the member to be coated is attracted to the second fixing part so as to be fixed in the reservoir. Accordingly, in the dip coating device of the present invention, even when the member to be coated receives buoyancy in the coating material within the reservoir, the member to be coated remains fixed to the second fixing part while being held by the first fixing part, so that the member to be coated hardly moves within the reservoir. Additionally, the dip coating device of the present invention suppresses attachment of a coating material to a supporting member which engages with, for example, a comb-shaped fixing member for each dipping operation of a member to be coated as in a conventional dip coating device, resulting in increasing a utilization ratio of the coating material.

(First Embodiment)

A dip coating device 10(10A) according to a first embodiment of the present invention is explained referring to FIGS. 1 and 2. FIG. 1 is a side view (a partial cross-sectional view) when a member to be coated is dipped into the coating material, and FIG. 2 is a side view (a partial cross-sectional view) when the member to be coated is pulled up. The dip coating device 10A comprises a reservoir 30, a first fixing part 40 and a second fixing part 50.

(1) Member to be Coated

First, description will be made of the member to be coated 20 which is to be coated with a coating material 70 by the dip coating device 10. The member to be coated 20 is a member at least an outer surface of which is to be coated with the coating material 70, and examples of the member include a container and a tubular body made of resin, glass, or metal. The container is a member which houses various kinds of gases, liquids, solids. The tubular body is a tubular member having a lumen and can be configured to have, for example, a single tube structure, a multiple-tube structure including a plurality of concentrically formed tubes having different diameters, or a combination thereof.

The dip coating device 10 of the present invention is capable of fixing a position of the member to be coated 20 in the reservoir 30 by a magnetic attractive force generated between the first fixing part 40 and the second fixing part 50. Therefore, the present invention is suitable for coating the member to be coated 20 susceptible to buoyancy in the coating material 70. Further, since the dip coating device 10 of the present invention enables uniformness of a coated film thickness to be increased, the device is suitable for coating precision equipment and medical products in particular requiring stable product quality.

In the present invention, the member 20 to be coated is preferably a medical tubular body. The medical tubular body is a tube made of resin or metal, or a combination thereof, and is used as, for example, a catheter, a resin stent, a drainage tube, or the like. Many of medical tubular bodies are made of resin and have a lumen and therefore have a lower specific gravity with respect to the coating material 70. As a result, the medical tubular body in the coating material 70 receives buoyancy to float, comes into contact with a side wall of the reservoir 30 which stores the coating material 70, or slides in the coating material 70, so that a position of the medical tubular body cannot be determined with ease. However, as will be described later, with the dip coating device 10 of the present invention, even when the member to be coated 20 is susceptible to buoyancy, a position thereof in the reservoir 30 can be fixed with ease.

The medical tubular body is preferably a medical catheter. Since the dip coating device 10 of the present invention enables coating of the member to be coated 20 with ease, productivity of the medical catheter can be increased. Additionally, the medical catheter may be a balloon catheter. This is because the dip coating device 10 of the present invention can be suitable for the member to be coated 20 having large buoyancy.

(2) Coating Material

As the coating material 70 to be coated on the member to be coated 20, any liquid or a liquid material can be used, including, for example, silicone resin, urethane resin, acrylic resin, fluorocarbon polymers, or a combination thereof which is diluted with a solvent. The type of the coating material 70 can be appropriately selected in view of functions required for the member to be coated 20, for example, improved slidability of the member to be coated, excellent washability of the reservoir, ease of handling, and protection and reinforcement of the member to be coated. Additionally, when a member to be coated is for medical use, the type of the coating material 70 can be appropriately selected in view of harmlessness to a human body, antithrombogenic, and among them, in a case of coating with a medicine, treatment effect, or the like.

(3) Reservoir

The reservoir 30 that stores a coating material 70, and has a wall 31. The wall 31 comprises a bottom wall 32 and a side wall 33. A shape of the reservoir 30 is not particularly limited and only needs to have an opening part 34 for taking in or out the member to be coated 20 and the first fixing part 40 into or from the reservoir 30. Additionally, the opening part 34 of the reservoir 30 may be provided with a lid (not shown) for suppressing foreign matters from entering the coating material 70. In a direction (the Z direction) perpendicular to a liquid surface (the X-Y direction) of the coating material 70, the opening part 34 is preferably provided in an upper part of the side wall 33 of the reservoir 30 and is more preferably provided on an upper end part of the side wall 33.

As shown in FIGS. 1 and 2, a part of the side wall 33 of the reservoir 30 is inclined with respect to the direction (the Z direction) perpendicular to the liquid surface (the X-Y direction) of the coating material 70. In FIGS. 1 and 2, θ shows an angle of inclination. When the side wall 33 of the reservoir 30 is inclined, the opening part of the reservoir 30 can be increased in an area, the opening part serving for dipping the member to be coated 20 into the coating material 70 or for pulling up the member to be coated 20 from the coating material 70. As a result, the dip coating device of the present invention allows a spaced distance between the member to be coated 20 and the side wall 33 to be increased, so that the member to be coated 20 and the side wall 33 hardly come into contact with each other. This suppresses generation of a coating failure of the member to be coated 20 due to contact between the member to be coated 20 and the side wall 33.

Since when the angle of inclination θ is too small, the member to be coated 20 might come into contact with the side wall 33, a lower limit value of the angle of inclination θ is preferably 5°, more preferably 10°, and further preferably 15°. On the other hand, when the angle of inclination θ is too large, an area of the reservoir 30 in the opening part 34 becomes so large that a device size in the X-Y direction is increased, and therefore an upper limit value of the angle of inclination θ is preferably 70°, more preferably 60°, and further preferably 50°.

Additionally, in order to suppress generation of a coating failure of the member to be coated 20, the reservoir 30 preferably has a cross section at the upper side (the opening 34 side) larger than a cross section at the lower side (the bottom wall 32 side) in the direction (the Z direction) perpendicular to the liquid surface (the X-Y direction) of the coating material 70. The coating material 70 in the reservoir 30 preferably has a first cross section with an inner diameter larger than an inner diameter of a second cross section on a side closer to the bottom wall in relation to the first cross section, the first cross section being parallel to a liquid surface of the coating material and close to the liquid surface. In other words, the reservoir 30 preferably has a upper cross section with an inner diameter larger than an inner diameter of a lower cross section. This allows an opening part of the reservoir to have an increased area, the opening part serving for dipping the member to be coated into the coating material or for pulling up the member to be coated from the coating material. As a result, the dip coating device of the present invention allows a spaced distance between the member to be coated and the side wall to be increased, so that the member to be coated and the side wall hardly come into contact with each other.

A material of the reservoir 30 is not particularly limited, and among usable are, for example, metal materials including stainless steel such as SUS 304, SUS 316, SUS 420, and SUS 430, polymeric materials such as polypropylene (PP), polyethylene (PE), and polytetrafluoroethylene (PTFE), a permanent magnet such as a neodymium magnet or a samarium-cobalt magnet having a high magnetic flux density, an electromagnet, or a combination thereof. Among them, when the first fixing part 40 and the second fixing part 50 are moved while being in contact with the wall 31 of the reservoir 30, the reservoir 30 is preferably made of a material having a small frictional resistance and excellent sliding properties. It is possible to use, as the reservoir 30, for example, a tank with a surface covered with fluorocarbon polymers such as PTFE, the surface being formed of stainless steel such as SUS 304. In order to ensure intensity of a magnetic attractive force while preventing a magnetic field between the first fixing part 40 and the second fixing part 50 from being shielded as possible, the reservoir 30 preferably uses no magnetic body as a material, and the reservoir 30 also preferably has a small thickness.

As shown in FIGS. 1 and 2, the side wall 33 of the reservoir 30 preferably has a thick part 35. Since this enables reduction in intensity of a magnetic attractive force acting between the first fixing part 40 and the second fixing part 50 in the thick part 35 of the reservoir 30, this makes it easy to take out the member to be coated 20 and the first fixing part 40 from the reservoir 30. The thick part 35 is preferably formed so as to become thicker from a lower part of the reservoir 30 toward an upper part of the reservoir 30 in a direction perpendicular to a liquid surface of the coating material. In particular, as shown in FIGS. 1 and 2, the bottom wall side of the thick part 35 is more preferably formed so as to become thicker from a lower part of the reservoir 30 toward an upper part of the reservoir 30. Since this prevents a distance between the first fixing part 40 and the second fixing part 50 from being rapidly increased, the first fixing part 40 and the second fixing part 50 can be smoothly pulled away. Additionally, the dip coating device of the present invention suppresses shock or vibration to be applied to the first fixing part 40 to a small level when the second fixing part 50 passes through the thick part 35, thereby enabling the coating material 70 to be coated on the member to be coated 20 to have a uniform thickness.

(4) First Fixing Part

The first fixing part 40 holds the member to be coated 20 in the reservoir 30, and magnetically attracts to a second fixing part 50 which will be described below. A shape of the first fixing part 40 can be appropriately set in the following manner according to a specific gravity of the member to be coated 20 with respect to the coating material 70 or a shape of the member to be coated 20. The first fixing part 40 may be a fixing member. Specifically, the first fixing part 40 is provided on a first fixing member.

Since when a specific gravity of the member to be coated 20 with respect to the coating material 70 is large, buoyancy of the member to be coated 20 is small to facilitate fixing of the position of the member to be coated 20 in the reservoir 30, it is only necessary to fix at least a part of the member to be coated 20. For example, the first fixing part 40 may have a grasping part for grasping other part outside a coating range of the member to be coated 20 such that the member to be coated 20 is fixed by grasping.

On the other hand, when the specific gravity of the member to be coated 20 with respect to the coating material 70 is small, the member to be coated 20 might receive buoyancy to move in the coating material 70. Accordingly, when the specific gravity of the member to be coated 20 with respect to the coating material 70 is small, the member to be coated 20 is preferably fixed in its entirety, and when the member to be coated 20 is a tubular body, the first fixing part 40 is preferably inserted into a lumen of the tubular body. Since this enables the specific gravity of the member to be coated 20 with respect to the coating material 70 to be substantially large, the member to be coated 20 is less likely to move in the reservoir 30, resulting in facilitating fixing of the position thereof.

When the member to be coated 20 is a tubular body, the first fixing part 40 preferably is a bar-shaped body (bar shape). This prevents the member to be coated 20 from being crimpled and enables the same to be fixed. The bar-shaped body, which is a bar-shaped member to be inserted into the lumen of the tubular body, receives buoyancy in the coating material 70 to prevent the tubular body from bending. In general, although when the member to be coated 20 is pulled up from the liquid surface of the coating material 70, the coating material 70 attaches to the outer surface of the member to be coated 20, disposing an axis direction of the member to be coated 20 to be perpendicular to the liquid surface (the X-Y direction) of the coating material 70 makes the film thickness of the coated film to be uniform. Therefore, when the member to be coated 20 has an elastic tubular body, a bar-shaped body is preferable as a member for holding the tubular body in order to pull up the member to be coated 20 from the coating material 70 while maintaining the tubular body as straight as possible so as to be perpendicular to the liquid surface. Additionally, since when the bar-shaped body is being inserted in the lumen of the tubular body, the coating material 70 entering the lumen of the tubular body can be reduced, attachment of the coating material 70 to an inner surface of the tubular body can be suppressed.

Although a shape of the bar-shaped body is not particularly limited as long as the shape allows insertion into the lumen of the tubular body, the shape is preferably columnar or polygonal columnar for facilitating production. Additionally, for suppressing stress concentration when the bar-shaped body and the tubular body come into contact with each other, the bar-shaped body is preferably columnar or elliptic cylindrical. Further, for facilitating insertion of the bar-shaped body into the tubular body, a long axis direction of the bar-shaped body is preferably parallel to a long axis direction of the tubular body.

The bar-shaped body may have a flow path passing through along the axis direction. Specifically, the bar-shaped body may have a shape with a groove formed on a surface of a pillar-shaped body having a tubular-shape, a columnar-shape, a polygonal columnar-shape, or the like. When the tubular body having inserted the bar-shaped body having a flow path is dipped into the coating material 70 in the reservoir 30 in this manner, by flowing gas through the flow path from an upper side to a lower side in the Z direction of the reservoir 30, the coating material 70 to enter the lumen of the tubular body from the lower side in the Z direction of the tubular body can be pushed out, so that attachment of the coating material 70 to the inner surface of the tubular body can be suppressed.

In a case where the first fixing part 40 is a bar-shaped body, for further suppressing attachment of the coating material 70 to the inner surface of the tubular body, with the bar-shaped body inserted in the tubular body, an upper limit value of a distance from the inner surface of the tubular body to an outer surface of the first fixing part 40 is preferably 150 µm, 140 µm, or 130 µm. On the other hand, in view of facilitating insertion of the first fixing part 40 into the lumen of the tubular body, with the bar-shaped body inserted in the tubular body, a lower limit value of a distance between the inner surface of the tubular body and the outer surface of the first fixing part 40 is preferably 15 µm, more preferably 20 µm, and further preferably 30 µm. The distance from the inner surface of the tubular body to the outer surface of the first fixing part 40 is preferably within the above range when the distance is constant in the entire periphery of the first fixing part 40 or when the distance is not constant.

(5) Second Fixing Part

The second fixing part 50 is provided on a wall 31 of the reservoir 30, and magnetically attracts to the first fixing part 40. Therefore, even when the member to be coated 20 receives buoyancy in the coating material 70, the member to be coated 20 is attracted to the second fixing part 50 so as to be fixed in the reservoir 30. Accordingly, even when the member to be coated 20 receives buoyancy in the coating material 70 within the reservoir 30, the member to be coated 20 remains fixed to the second fixing part 50 while being held by the first fixing part 40, so that the member to be coated 20 hardly moves within the reservoir 30. Additionally, this suppresses attachment of the coating material to a supporting member which engages with, for example, a comb-shaped fixing member for each dipping operation of a member to be coated as in a conventional dip coating device, resulting in increasing a utilization ratio of the coating material. The second fixing part 50 may be a fixing member. Specifically, the second fixing part 50 may be provided on a second fixing member.

Although the second fixing part 50 may be provided at an inner side or an outer side of the wall 31 of the reservoir 30, the second fixing part 50 is preferably provided at the outer side of the wall 31 in terms of an increase in an amount of the coating material 70 which can be stored in the reservoir 30, and in terms of prevention of attachment of the coating material 70 to the second fixing part 50. Additionally, the second fixing part 50 may be directly or indirectly provided on the wall 31 of the reservoir 30. The second fixing part 50 may be directly attached to the wall 31 of the reservoir 30 or indirectly attached to the wall via an adhesive or the like. The wall 31 of the reservoir 30 and the second fixing part 50 may be integrally formed. In this case, it is preferable that the first fixing part 40 has a magnet, and the wall 31 is formed of a material which is attracted to the magnet. In the present invention, "the wall of the reservoir and the second fixing part are integrally formed" means that the reservoir is formed of a material which generates a magnetic attractive force between the reservoir and the first fixing part.

At least one of the first fixing part 40 and the second fixing part 50 is preferably provided with a magnet. When at least one of the first fixing part 40 and the second fixing part 50 is provided with a magnet, a magnetic attractive force can be generated between the first fixing part 40 and the second fixing part 50. Since the magnet needs to have a sufficient magnetic force even via the side wall 33 of the reservoir 30, a permanent magnet having a high magnetic flux density can be used such as, a neodymium magnet or a samarium-cobalt magnet. One of the first fixing part 40 and the second fixing part 50 may be a magnet and the other may be formed of a magnetic material which attracts the magnet. Specifically, when the first fixing part 40 is a magnet, a metal material such as stainless steel can be used as the second fixing part 50, for example, SUS 304, SUS 316, SUS 420, or SUS 430 which is attracted to the magnet each other. Additionally, when the second fixing part 50 is a magnet, a metal material such as stainless steel can be used as the first fixing part 40, for example, SUS 304, SUS 316, SUS 420, or SUS 430 which is attracted to the magnet each other.

The magnet is preferably an electromagnet. In a case where the magnet is an electromagnet, intensity of the magnetic attractive force can be adjusted.

The dip coating device 10 may be provided with a driver 60 having a first driving part 61 to be connected to the first fixing part 40, a first shaft part 62 which supports the first driving part 61, a connecting part 63 which connects the second fixing part 50 and the first driving part 61, and a guiding part 64 which guides a path of the second fixing part 50.

In FIGS. 1 and 2, an upper part of the first fixing part 40 is connected to the first driving part 61. An axis direction of the first shaft part 62 which supports the first driving part 61 is disposed to be parallel to an inclined part of the side wall 33 of the reservoir 30. Therefore, by moving the first driving part 61 along the first shaft part 62, the first fixing part 40 connected to the first driving part 61 can be moved along the inclination of the reservoir 30.

As shown in FIGS. 1 and 2, the first driving part 61 which moves the first fixing part 40 is preferably connected also to the second fixing part 50. Since the first fixing part 40 and the second fixing part 50 between which a magnetic attractive force is generated can be operated in associated with each other, the position of the member to be coated 20 can be easily fixed over the entire Z direction of the reservoir 30.

In FIGS. 1 and 2, the first driving part 61 and the second fixing part 50 are connected via the connecting part 63.

In order to suppress the second fixing part 50 from unintentionally separating from the reservoir 30 to weaken a magnetic attractive force, a dip coating device 10A can be provided with the guiding part 64 which guides the path of the second fixing part 50. For suppressing the magnetic attractive force from weakening, the guiding part 64 is preferably inclined at least partly, and is more preferably inclined in parallel to the side wall 33 of the reservoir 30.

Hereinafter, a dip coating device which has a mode different from the dip coating device 10A as shown in FIGS. 1 and 2 is explained referring to FIGS. 3 to 8. Note that the same description as the above description are omitted in FIGS. 3 to 8. FIGS. 3 to 8 and 10 are side views (a partial cross-sectional view) of the dip coating device, and FIG. 9 is a perspective view (a partial cross-sectional view) of the dip coating device.

(Second Embodiment)

A dip coating device 10(10B) which is provided with no inclination on the side wall 33 of the reservoir 30 according to a second embodiment is explained referring to FIGS. 3 and 4. FIG. 3 is a side view (a partial cross-sectional view) when the member to be coated 20 is dipped into the coating material 70, and FIG. 4 is a side view (a partial cross-sectional view) when the member to be coated 20 is pulled up.

For suppressing the side wall 33 of the reservoir 30 and the member to be coated 20 from coming into contact with each other, an outer diameter of a first fixing part 40 of a dip coating device 10B may not be uniform in an axis direction. With the first fixing part 40 of the dip coating device 10B being a bar-shaped body (bar shape), an outer diameter at one end part of the bar-shaped body is preferably larger than an outer diameter at the other end part thereof, and an outer diameter on the side of a bottom wall 32 is preferably larger than an outer diameter on the side of an opening part 34.

Specifically, the first fixing part 40 of the dip coating device 10B is preferably provided with a bulge part projecting toward a side wall 33. This makes the bulge part 41 first comes into contact with the side wall 33 of the reservoir 30 even when the first fixing part 40 comes close to the side wall 33. This allows to ensure a spaced distance between the member to be coated 20 and the side wall 33 to a certain extent, so that the member to be coated 20 is less likely to come into contact with the side wall 33, resulting in preventing generation of a coating failure due to contact between the member to be coated 20 and the side wall 33. The bulge part 41 is preferably provided at one end part of the first fixing part 40 and is more preferably provided at the one end part of the first fixing part 40 disposed in proximity to the bottom wall 32.

In FIGS. 3 and 4, the bulge part 41 of the first fixing part 40 is formed to be spherical with a diameter larger than an outer diameter of the member to be coated 20 which is a tubular body. When the bulge part 41 is formed to be spherical, the member to be coated 20 is less likely to come into contact with the side wall 33 over the entire periphery, and thus preferable. The spherical bulge part 41 can be formed by melting one end part of the first fixing part 40 by laser or the like.

Although not shown, when the first fixing part 40 is a bar-shaped body, the bulge part 41 may be formed by bending one end part of the first fixing part 40 in one direction using a pressing machine or the like. Additionally, the bulge part 41 formed into a desired shape using laser or the like may be connected to the first fixing part 40.

Since in the dip coating device 10B, the side wall 33 of the reservoir 30 is provided with no inclination, a first driving part 61 moves to the same direction (the Z direction) as the first fixing part 40 and a second fixing part 50. Therefore, as compared with the first embodiment, the device can be reduced in size in the X-Y direction.

(Third Embodiment)

A dip coating device 10(10C) which is provided with no inclination on the side wall 33 of the reservoir 30 according to the third embodiment is explained referring to FIGS. 5 to 7. FIG. 5 is a side view (a partial cross-sectional view) when the member to be coated 20 is dipped into the coating material 70, FIG. 6 is a side view (a partial cross-sectional view) when the member to be coated 20 is pulled up, and FIG. 7 is a side view (a partial cross-sectional view) when the first fixing part 40 is pulled up.

As shown in FIGS. 5 to 7, the side wall 33 of the reservoir 30 of the dip coating device 10C is preferably provided with a projection part projecting toward inside of the reservoir 30. This facilitates the projection part 36 to first come into contact with the reservoir 30 even when the first fixing part 20 comes close to the side wall 33. Since it is therefore possible to ensure a spaced distance between the member to be coated 20 and the side wall 33 to a certain extent, the member to be coated 20 is less likely to come into contact with the side wall 33, resulting in preventing a coating failure due to contact between the member to be coated 20 and the side wall 33.

The projection part 36 is preferably formed in a lower part of the reservoir 30 when the reservoir 30 is divided into three parts in the up-down direction (the Z direction). This is because in a case where the projection part 36 is formed in an upper part of the reservoir 30, when the member to be coated 20 is moved into the reservoir 30, the first fixing part 40 might come into contact with the projection part 36 before reaching a desired coating range.

Although the projection part 36 only needs to be provided at a part of a circumferential direction of the reservoir 30, the projection part 36 is more preferably provided over the circumferential direction of the reservoir 30 in order to reduce a risk that the reservoir 30 and the member to be coated 20 come into contact with each other.

In FIGS. 5 to 7, provision of a rectangular second fixing part 50 at an outer side of the projection part 36 of the reservoir 30 is more likely to cause contact with the first fixing part 40 at the projection part 36. Although FIGS. 5 to 7 show an example where the second fixing part 50 is provided at the outer side of the reservoir 30, the second fixing part 50 can be disposed at the inner side of the reservoir 30 so as to minimize a magnetic attractive force acting between the first fixing part 40 and the second fixing part 50.

Since in the dip coating device 10C, the second fixing part 50 is fixed to a wall 31 of the reservoir 30, it is not necessary to provide a driver for moving the second fixing part 50. Additionally, since the side wall 33 of the reservoir 30 is provided with no inclination similarly to the second embodiment, the device can be reduced in size in the X-Y direction as compared with the first embodiment.

The dip coating device 10C is provided with a driver 60 for moving the member to be coated 20 and the first fixing part 40 to the outside or inside of the reservoir 30. The driver 60 has a first driving part 61 connected to the member to be coated 20, a first shaft part 62 which supports the first driving part 61, a second driving part 65 connected to the first fixing part 40, and a second shaft part 66 which supports the second driving part 65.

(Fourth Embodiment)

FIG. 8 is a side view (a partial cross-sectional view) of the dip coating device according to a fourth embodiment of the present invention. A dip coating device 10(10D) in FIG. 8 is a configuration example where the first fixing part 40 and the reservoir 30 magnetically attract to each other. Specifically, the configuration example is a case where the reservoir and the second fixing part are integrally formed. As shown in FIG. 8, the dip coating device 10D for coating a member to be coated 20 with a coating material 70, comprises a reservoir 30 that stores a coating material 70, and a first fixing part 40 that holds a member to be coated 20, wherein the first fixing part 40 and the reservoir 30 magnetically attract to each other. The dip coating device 10D generates a magnetic attractive force between the first fixing part 40 and the reservoir 30 to enable simplification of a structure of the device. Here, at least one of the first fixing part 40 and the reservoir 30 only needs to be provided with a magnet, and the magnet may be an electromagnet. In this case, as the other, a metal material such as stainless steel can be used, for example, SUS 304, SUS 316, SUS 420, or SUS 430 which is attracted to the magnet each other.

(Fifth Embodiment)

FIG. 9 is a perspective view (a partial cross-sectional view) of the dip coating device according to a fifth embodiment of the present invention. A dip coating device 10(10E) in FIG. 9 is a configuration example where a plurality of the members to be coated 20 are coated together. As shown in FIG. 9, it is preferable that a plurality of the first fixing parts 40(40A, 40B and 40C) which are arranged in parallel with each other holds a plurality of the members to be coated 20(20A, 20B and 20C) which are preferably arranged in parallel with each other respectively. By configuring the first fixing part 40 in this manner, this enables coating, with a coating material 70, of even a plurality of members 20 to be coated provided in parallel to each other, thus productivity can be increased.

(Sixth Embodiment)

FIG. 10 is a side view (a partial cross-sectional view) of the dip coating device according to a sixth embodiment of the present invention, and is a configuration example where the first fixing part 40 and a buffer member 55 magnetically repel each other. In a dip coating device 10(10F), it is preferable that the first fixing part 40 is provided with the magnet, and the reservoir 30 is composed of stainless steel which is attracted to the magnet. As shown in FIG. 10, in the dip coating device 10F, it is preferable that the side wall 33 of the reservoir 30 is provided with the buffer member 55, and the first fixing part 40 and the buffer member 55 magnetically repel each other. This enables reduction in a risk that in a region where a buffer member 55 is provided, the first fixing part 40 comes into contact with the reservoir 30. The buffer member 55 is preferably disposed above the bottom wall 32 of the reservoir 30. In FIG. 10, although the buffer member 55 is provided at an inner side of the side wall 33, the buffer member 55 may be provided at an outer side of the side wall 33 (not shown). Such a mode of provision of the buffer member 55 is suitably used when the reservoir 30 having the side wall 33 without inclination is used as in the above second to fourth embodiments.

The present invention is preferably a medical tubular body produced by the above dip coating device. Since a medical tubular body produced by the above dip coating device is uniformly coated with a coating material 70, the coating material 70 fully exhibits function thereof, and an effect of protecting the tubular body by a coated film is also expected.

2. Method for Producing Coated Member

The present invention includes a method for producing a coated member obtained by dip coating a member to be coated with a coating material, comprising the steps of: fixing a member to be coated to a first fixing part; dipping the member to be coated into a reservoir in which a coating material is stored; moving the first fixing part close to a second fixing part which is directly or indirectly provided on a wall of the reservoir and capable of generating a magnetic attractive force with the first fixing part; separating the first fixing part from the second fixing part; and pulling up the member to be coated out of the reservoir in which the coating material is stored. The method for producing a coated member according to a first embodiment of the present invention is explained referring to FIGS. 1, 2 and 11 showing a configuration of the dip coating device according to the first embodiment. FIG. 11 is a cross-sectional view when a first fixing part 40 which is a rod having a circular cross section perpendicular to the axis direction (the Z direction) is inserted into a lumen of a member to be coated 20.

(1) Step of Fixing Member to be Coated to First Fixing Part

The member to be coated 20 is fixed to the first fixing part 40. Fixing of the member to be coated 20 to the first fixing part 40 is conducted in a state where a magnetic attractive force acting between the first fixing part 40 and a second fixing part 50 is weak enough, i.e., in a state where the first fixing part 40 and the second fixing part 50 are spaced.

In FIG. 11, the member to be coated 20 is a medical tubular body having a multiple-tube structure, and is a balloon catheter 21 with a balloon part 22 formed in a part of the multiple-tube structure. The first fixing part 40 is inserted into a lumen of the balloon catheter 21 so as to expose a part of the first fixing part 40 on the side of the reservoir 30 from the balloon catheter 21. Thus, it is preferable that the member to be coated 20 is a tubular body, and in the present step of fixing the member to be coated 20 to the first fixing part 40, the first fixing part 40 is inserted into the lumen of the tubular body. Since insertion of the first fixing part 40 into the lumen of the tubular body prevents the coating material 70 from easily entering the lumen of the tubular body, attachment of the coating material 70 to the lumen of the tubular body can be suppressed.

(2) Step of Dipping Member to be Coated into Reservoir in which Coating Material is Stored As shown in FIG. 1, the member to be coated 20 is dipped into a reservoir 30 in which a coating material 70 is stored. Specifically, in FIG. 1, by moving the first driving part 61 along the first shaft part 62 in an A direction in FIG. 1, the first fixing part 40 and the member to be coated 20 also move along the side wall 33 of the reservoir 30 in the A direction, resulting in dipping the member to be coated 20 into the coating material 70 in the reservoir 30.

(3) Step of Moving First Fixing Part Close to Second Fixing Part which is Directly or Indirectly Provided on Wall of Reservoir and Capable of Generating Magnetic Attractive Force with First Fixing Part The first fixing part 40 is moved close to the second fixing part 50 which is directly or indirectly provided on the wall 31 of the reservoir 30 and capable of generating a magnetic attractive force with the first fixing part 40. The member to be coated 20 which is fixed to the first fixing part 40 is attracted by the second fixing part 50 and fixed in the reservoir 30.

Regarding the above steps including: (1) the step of fixing the member to be coated to the first fixing part; (2) the step of dipping the member to be coated in the reservoir in which a coating material is stored; and (3) the step of moving the first fixing part close to the second fixing part which is directly or indirectly provided on the wall of the reservoir and capable of generating a magnetic attractive force with the first fixing part, after any one of the steps is completed, the other may be executed, or may be executed simultaneously or at different times.

Since the method for producing a coated member of the present invention includes the step of moving the first fixing part 40 close to the second fixing part 50 which is capable of generating a magnetic attractive force with the first fixing part 40, the first fixing part 40 and the second fixing part 50 magnetically attract to each other while the member to be coated 20 remains fixed, and thus the member to be coated 20 hardly moves within the reservoir 30. Accordingly, since the method for producing a coated member of the present invention enables a position of the member to be coated 20 to be fixed in the reservoir 30, the method is also suitably used when the member to be coated 20 is susceptible to buoyancy. Additionally, this suppresses attachment of a coating material to a supporting member which engages with, for example, a comb-shaped fixing member for each dipping operation of a member to be coated as in a conventional dip coating method, resulting in increasing a utilization ratio of the coating material.

It is preferable that at least one of the first fixing part 40 and the second fixing part 50 is provided with a electromagnet, and the method further comprises the step of generating a magnetic attractive force between the first fixing part 40 and the second fixing part 50 by the electromagnet after the step of moving the first fixing part close to the second fixing part which is directly or indirectly provided on the wall of the reservoir and capable of generating a magnetic attractive force with the first fixing part. When at least one of the first fixing part 40 and the second fixing part 50 is provided with a magnet, intensity of a magnetic attractive force can be adjusted. Additionally, by generating a magnetic attractive force after the step of moving the first fixing part close to the second fixing part, it is possible to suppress the first fixing part 40 and the second fixing part 50 from being attracted to each other while a distance between the first fixing part 40 and the second fixing part 50 is drastically reduced. This enables reduction in shock or vibration to be applied to the coating material 70, so that a thickness of the coating material 70 to be coated on a member to be coated 20 can be uniform.

(4) Step of Separating First Fixing Part from Second Fixing Part

When the member to be coated 20 has dipped in a desired coating range, the first fixing part 40 is separated from the second fixing part 50. Accordingly, the state of the first fixing part 40 and the second fixing part 50 being fixed is released.

(5) Step of Pulling Up Member to be Coated Out of Reservoir in which Coating Material is Stored As shown in FIG. 2, the first fixing part 40 is moved in a B direction to pull up the member to be coated 20 out of the reservoir 30 in which the coating material 70 is stored, and the first fixing part 40 and the second fixing part 50 are spaced until a magnetic attractive force therebetween is weakened. In a case where the reservoir 30 is provided with a thick part 35 as shown in FIG. 2, the first fixing part 40 and the second fixing part 50 can be spaced from each other by the thick part 35 of the reservoir 30 at which a magnetic attractive force between the first fixing part 40 and the second fixing part 50 is weakened.

Regarding the above steps including: (4) the step of separating the first fixing part from the second fixing part; and (5) the step of pulling up the member to be coated out of the reservoir in which the coating material is stored, after any one of the steps is completed, the other may be executed, or may be executed simultaneously or at different times.

The coated member is obtained by coating the member to be coated 20 with a coating material 70 in this manner. The method for producing a coated member of the present invention suppresses attachment of a coating material to a supporting member which engages with, for example, a comb-shaped fixing member for each dipping operation of a member to be coated as in a conventional dip coating device, resulting in increasing a utilization ratio of the coating material.

This application claims the benefit of the priority date of Japanese patent application No. 2015-92285 filed on Apr. 28, 2015. All of the contents of the Japanese patent application No. 2015-92285 filed on Apr. 28, 2015, are incorporated by reference herein.

REFERENCE SIGNS LIST

10, 10A, 10B, 10C, 10D, 10E and 10F: a dip coating device
20: a member to be coated
21: a balloon catheter
22: a balloon part
30: a reservoir
31: a wall
32: a bottom wall
33: a side wall
34: an opening part
35: a thick part
36: a projection part
40: a first fixing part
41: a bulge part
50: a second fixing part
55: a buffer member
60: a driver
61: a first driving part
62: a first shaft part
63: a connecting part
64: a guiding part
65: a second driving part
66: a second shaft part
70: a coating material

The invention claimed is:

1. A dip coating device or coating a medical tubular body to be coated with a coating material, comprising:
    a reservoir for storing a coating material;
    a first fixing member for holding a medical tubular body to be coated, the first fixing member having a first affixing part;
    a second affixing part directly or indirectly provided on a wall of the reservoir, wherein the second affixing part is movable: and
    a driving part that moves the second affixing part,
    wherein
    the first affixing part and the second affixing part are configured to be magnetically attracted to each other,
    when the first affixing part and the second affixing part are magnetically attracted to each other, the first affixing part is in direct contact with the reservoir,
    the first affixing part is provided with a bulge part projecting toward a side wall of the reservoir, the bulge part of the first affixing part provided at one end part of the first affixing part disposed in proximity to a bottom wall of the reservoir, an outer diameter of the bulge part of the first affixing part is larger than an outer diameter of the medical tubular body, and the first fixing member has a columnar shape or a polygonal columnar shape.

2. The dip coating device according to claim wherein the second affixing part is provided on a second fixing member.

3. The dip coating device according to claim 1, wherein the reservoir and the second affixing part are integrally formed.

4. The dip coating device according to claim 1, wherein a part of the side wall of the reservoir is inclined with respect to a direction perpendicular to a liquid surface of the coating material.

5. The dip coating device according to claim 1, wherein the side wall of the reservoir has a thick part being thicker than remaining portions of the side wall.

6. The dip coating device according to claim 5, wherein the thick part is formed so as to become thicker from a lower part of the reservoir toward an upper part of the reservoir in a direction perpendicular to a liquid surface of the coating material.

7. The dip coating device according, to claim 1, wherein the side wall of the reservoir is provided with a projection part projecting toward inside of the reservoir.

8. The dip coating device according to claim 1, wherein at least one of the first affixing part and the second affixing part is provided with a magnet.

9. The dip coating device according to claim 8, wherein the magnet is an electromagnet.

10. The dip coating device according to claim 1, wherein the side wall of the reservoir is provided with a buffer member, and the first affixing part and the buffer member magnetically repel each other.

11. The dip coating device according to claim 1, comprising a plurality of the first fixing members which are arranged in parallel with each other, so that each of the first fixing member holds the medical tubular body to be coated and the medical tubular bodies are arranged in parallel with each other.

12. The dip coating device according to claim 1, wherein the medical tubular body is a medical catheter.

13. The dip coating device according to claim 1, wherein the medical catheter is a balloon catheter.

14. A medical tubular body produced by the dip coating device, according to claim 1.

15. A method for producing a coated medical tubular body obtained by dip coating a medical tubular body to be coated with a coating material, comprising the steps of:

fixing a medical tubular body to be coated to a first fixing member having a first affixing part;

dipping the medical tubular body to be coated into a reservoir in which a coating material is stored;

moving the first affixing part close to a second affixing part which is directly or indirectly provided on a wall of the reservoir and capable of generating a magnetic attractive force with the first affixing part, so that the first affixing part and the second affixing part magnetically attract to each other and the first affixing part is in direct contact with the reservoir;

separating the first affixing part from the second affixing part; and pulling up the medical tubular body coated out of the reservoir in which the coating material is stored, wherein the second affixing part is movable via a driving part, the first affixing part is provided with a bulge part projecting toward a side wall of the reservoir, the bulge part of the first affixing part is provided at one end part of the first affixing part disposed proximity to a bottom wall of the reservoir, and an outer diameter of the bulge part of the first affixing part is larger than an outer diameter of the medical tubular body.

16. The method for producing a coated medical tubular body according to claim 15, wherein at least one of the first affixing part and the second affixing part is provided with a electromagnet, and the method further comprises the step of generating a magnetic attractive force between the first affixing part and the second affixing part by the electromagnet after the step of moving the first affixing part close to the second affixing part.

17. The method for producing a coated medical tubular body according to claim 15, wherein the first affixing part is inserted into a lumen of the medical tubular body in the step of fixing the member to be coated to the first affixing part.

18. A dip coating device for coating a medical tubular body to be coated with a coating material, comprising:

a reservoir for storing a coating material;

a holding member for holding a medical tubular body to be coated, the holding member having a first affixing part:

a second affixing part directly or indirectly provided on an outer surface of a wall of the reservoir, wherein the second affixing part is movable: and a driving part that moves the second affixing part, wherein the first affixing part has a columnar shape or a polygonal columnar shape, the first affixing part is located inside the reservoir and the second affixing part is located outside the reservoir, so that the first affixing part and the second affixing part magnetically attract to each other via a wall of the reservoir and the first affixing part is in direct contact with the reservoir, the first affixing part is provided with a bulge part projecting toward a side wall of the reservoir, the bulge part of the first affixing part is provided at one end part of the first affixing part disposed in proximity to a bottom wall of the reservoir, and an outer diameter of the bulge part of the first affixing part is larger than an outer diameter of the medical tubular body.

* * * * *

UNITED STATES PATENT AND TRADEMARK OFFICE
CERTIFICATE OF CORRECTION

PATENT NO. : 10,625,298 B2
APPLICATION NO. : 15/570253
DATED : April 21, 2020
INVENTOR(S) : Takura Koda Page 1 of 1

It is certified that error appears in the above-identified patent and that said Letters Patent is hereby corrected as shown below:

In the Claims

Claim 1, Column 19, Line 2 - insert --is-- before "provided"
Claim 2, Column 19, Line 9 - insert --1-- after "claim"
Claim 7, Column 19, Line 27 - delete "," after "according"

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*